(12) United States Patent
Singh

(10) Patent No.: US 12,702,464 B2
(45) Date of Patent: Aug. 11, 2026

(54) CHEMICAL ABLATION THERAPY DELIVERY SYSTEM

(71) Applicant: Medtronic Ireland Manufacturing Unlimited Company, Dublin (IE)

(72) Inventor: Manoj Kumar Singh, Santa Rosa, CA (US)

(73) Assignee: Medtronic Ireland Manufacturing Unlimited Company, Dublin (IE)

( * ) Notice: Subject to any disclaimer, the term of this patent is extended or adjusted under 35 U.S.C. 154(b) by 319 days.

(21) Appl. No.: 18/549,703

(22) PCT Filed: Apr. 11, 2022

(86) PCT No.: PCT/EP2022/059626
§ 371 (c)(1),
(2) Date: Sep. 8, 2023

(87) PCT Pub. No.: WO2022/218922
PCT Pub. Date: Oct. 20, 2022

(65) Prior Publication Data

US 2024/0156508 A1 May 16, 2024

Related U.S. Application Data

(60) Provisional application No. 63/173,880, filed on Apr. 12, 2021.

(51) Int. Cl.

| | |
|---|---|
| ***A61B 18/06*** | (2006.01) |
| *A61B 18/00* | (2006.01) |
| *A61B 18/14* | (2006.01) |

(52) U.S. Cl.
CPC ...... *A61B 18/06* (2013.01); *A61B 2018/0022* (2013.01); *A61B 2018/00577* (2013.01); *A61B 2018/143* (2013.01)

(58) Field of Classification Search
CPC .......... A61B 18/06; A61B 2018/00214; A61B 2018/0022; A61B 2018/00232; A61B 2018/00238; A61B 2018/0025; A61B 2018/00255; A61B 2018/00273; A61B 2018/00279; A61B 2018/00285; A61B 2018/00577; A61B 2018/143; A61B 2018/00267; A61B 2018/00404; A61B 2018/00434; A61B 2018/00511;
(Continued)

(56) References Cited

U.S. PATENT DOCUMENTS

| | | | |
|---|---|---|---|
| 5,336,178 | A | 8/1994 | Kaplan et al. |
| 6,579,305 | B1 | 6/2003 | Lashinski |

(Continued)

FOREIGN PATENT DOCUMENTS

| | | |
|---|---|---|
| EP | 1188417 A2 | 3/2002 |

OTHER PUBLICATIONS

International Preliminary Report on Patentability from International Application No. PCT/EP2022/059626 dated Oct. 12, 2023, 9 pp.

(Continued)

*Primary Examiner* — Thomas A Giuliani
(74) *Attorney, Agent, or Firm* — Shumaker & Sieffert, P.A.

(57) ABSTRACT

A chemical ablation therapy delivery system includes an expandable element, a guide tube attached to the expandable element, and a needle movably disposed within the guide tube.

12 Claims, 16 Drawing Sheets

(58) Field of Classification Search
CPC .. A61B 2018/00994; A61B 2018/0275; A61B 2018/1472; A61M 25/104; A61M 25/0084; A61M 2025/0087; A61M 2025/0096
USPC ......... 606/20–23, 27, 28, 32, 34, 37, 39–41, 606/45–50; 607/96, 98, 99, 101, 104, 607/105, 113, 115, 116
See application file for complete search history.

(56) References Cited

U.S. PATENT DOCUMENTS 6,585,926 B1 7/2003 Mirzaee
7,959,630 B2 6/2011 Taimisto et al.
8,079,978 B2 * 12/2011 Hirszowicz ........... A61M 29/02 604/103.07
8,187,221 B2 5/2012 Bates
8,353,900 B2 1/2013 Jung et al.
8,465,752 B2 6/2013 Seward
8,728,074 B2 * 5/2014 West .................. A61B 18/1492 606/41
8,975,233 B2 3/2015 Stein et al.
8,992,817 B2 3/2015 Stamberg
9,370,644 B2 6/2016 Rocha-singh
10,004,458 B2 6/2018 Toth et al.
10,226,278 B2 * 3/2019 Fischell ................. A61B 18/00
10,271,873 B2 4/2019 Steingisser et al.
10,758,713 B2 9/2020 Wang et al.
2008/0140001 A1 6/2008 Globerman et al.
2009/0143705 A1 * 6/2009 Danek ................ A61B 18/1492 601/3
2012/0035588 A1 * 2/2012 Schoenle ........... A61M 25/1011 604/101.02
2012/0101490 A1 4/2012 Smith
2013/0030410 A1 1/2013 Drasler et al.
2014/0276608 A1 9/2014 Roorda et al.
2016/0143522 A1 * 5/2016 Ransbury ............. A61B 8/0841 600/116
2017/0007310 A1 * 1/2017 Rajagopalan ........ A61B 5/0036

OTHER PUBLICATIONS

International Search Report and Written Opinion of International Application No. PCT/EP2022/059626 dated Nov. 16, 2022, 17 pp.

* cited by examiner 314
322
322
300'
302
310'
312
314
320'
320'
318
316

300"
310"
314
322
322
302
312
314
318a
320"
320"
318b
316b
324
316a 330a
310a
302
312
314
346a
346a
314
340
344
342
342
344
324
318
316

354
352a
352b
86
302
88
354
354
316d
354

84
86
302
88
312d
354
354
86
316d

CHEMICAL ABLATION THERAPY DELIVERY SYSTEM

This application is a U.S. National Stage entry under 35 U.S.C. § 371 of International Application No. PCT/EP2022/059626, filed Apr. 11, 2022, which claims priority from and the benefit of U.S. Provisional Patent Application No. 63/173,880, filed on Apr. 12, 2021, the entire content of each of which is incorporated herein by reference.

FIELD

The present disclosure generally relates to the field of ablation of biological material of a patient and, more particularly, to chemical ablation of such materials.

BACKGROUND

The nerves that lead to a patient's kidneys are part of the patient's sympathetic nervous system. An overactive sympathetic nervous system has been identified as a mechanism that results in high blood pressure. Various modalities have been used to interrupt the signaling associated with a patient's renal nerves, and this therapy may be referred to as "denervation." Representative renal denervation modalities include RF energy, pulsed electrical energy, microwave energy, optical energy, ultrasound energy (e.g., intravascularly delivered ultrasound, and/or HIFU), direct heat energy, radiation (e.g., infrared, visible, and/or gamma radiation), cryo-therapeutic cooling, and chemical ablation.

SUMMARY

A number of what may be characterized as chemical ablation therapy delivery systems are presented herein. Each such system in delivered intravascularly, utilizes at least one expandable element (e.g., a balloon; a stent), and accommodates directing an appropriate ablation agent (e.g., encompassing at least one ablation agent and thereby encompassing a combination of different ablation agents) through a wall of the vessel, for instance in a controlled/targeted manner (including in relation to the volume of the ablation agent that is discharged at a given target location). Both the configuration of such a chemical ablation therapy delivery system and the use of such a chemical ablation therapy delivery system are within the scope of this Summary.

One aspect of a chemical ablation therapy delivery system in accordance with the introductory paragraph of this Summary utilizes an expandable element (e.g., a balloon or a stent), at least one guide tube that is appropriately attached (e.g., fixed, secured, or otherwise anchored) to the expandable element (e.g., such that a given guide tube moves with the expandable element, including when the expandable element moves from a delivery state or configuration to a deployed state or configuration; such that at least part of a given guide tube is at all times maintained in a stationary position relative to the expandable element, for instance a distal end or a distal end section of such a guide tube), and a needle (e.g., an ablation needle) that is movably disposed within the guide tube. Typically after the expandable element is disposed in its deployed state or configuration, the needle is advanced relative to its corresponding guide tube such that the needle protrudes beyond a distal end of the guide tube and passes through a wall of a vessel in which the expandable element is disposed. An ablation agent may then be directed through the needle to discharge the ablation agent into an extravascular target location.

A number of implementations may be utilized for the above-described chemical ablation therapy delivery system. One is that one or more guide tubes may be directed into the interior of the expandable element and may be appropriately attached to the expandable element (e.g., a distal end of a given guide tube may be fixed or anchored to the expandable element). Another is that one or more guide tubes may be disposed on an exterior of the expandable element. Yet another is that the expandable element may be in the form of an outer expandable element and an inner expandable element, with one or more guide tubes being disposed between the outer expandable element and the inner expandable element and with each such guide tube being appropriately attached to the outer expandable element. The expandable element may also be in the form of an inflatable tube, and one or more guide tubes may be disposed on an exterior of such an inflatable tube, within an interior of such an inflatable tube, or both (but with each such guide tube being appropriately attached to the inflatable tube).

One aspect of a chemical ablation therapy delivery system in accordance with the introductory paragraph of this Summary utilizes an expandable element (e.g., a balloon or a stent), and at least one fluid delivery tube/conduit or ablation tube/conduit that is appropriately attached (e.g., fixed, secured, or otherwise anchored) to the expandable element (e.g., such that at least part of the fluid delivery tube moves with the expandable element, including when the expandable element moves from a delivery state or configuration to a deployed state or configuration). Each fluid delivery tube includes at least one injector (e.g., a spike) that extends from an outer perimeter of the corresponding fluid delivery tube, is fluidly interconnectable or is at all times fluidly interconnected with the corresponding fluid delivery tube, and protrudes beyond an outer perimeter of the expandable element. Disposing the expandable element in its deployed state or configuration directs at least one of the injectors through a wall of a vessel in which the expandable element is disposed. An ablation agent may then be directed through the injector(s) to discharge the ablation agent into an extravascular target location.

A number of implementations may be utilized for the above-described chemical ablation therapy delivery system. One is that one or more fluid delivery tubes may be positioned on an exterior surface of the expandable element. Another is that one or more fluid delivery tubes may be positioned on an interior surface of the expandable element. Any appropriate manner of delivering an ablation agent to each fluid delivery tube may be utilized.

One aspect of a chemical ablation therapy delivery system in accordance with the introductory paragraph of this Summary utilizes an inflatable tube. At least one injector is separately attached to the inflatable tube, where each injector is fluidly interconnectable or is at all times fluidly interconnected with an interior of the inflatable tube. Disposing the inflatable tube in its deployed state or configuration disposes at least one injector in interfacing relation with a wall of a vessel in which the inflatable tube is disposed, directs at least one injector through a wall of a vessel in which the inflatable tube is disposed, or both. An ablation agent may then be directed through the injector(s) to ultimately discharge the ablation agent into an extravascular target location.

The above-noted inflatable tube may be characterized as having a first end and a second end that is spaced from this first end, as well as an outer sidewall and an inner sidewall that each extend between these first and second ends and that are spaced from one another. A given injector incorporated by the inflatable tube may include one or more discharge ports for directing an ablation agent through a wall of a vessel in which the inflatable tube is disposed (e.g., when positioned against or in proximity to this wall). A given injector incorporated by the inflatable tube may be in the form of a spike having one or more discharge ports, where such an injector is directed through a wall of a vessel in which the inflatable tube is disposed in response to inflation of the inflatable tube and that discharges the ablation agent into an extravascular target location.

Further disclosed herein are embodiments of chemical ablation therapy delivery systems, wherein one aspect of such a system utilizes an expandable element, at least one guide tube that is fixed, secured, or otherwise anchored to the expandable element, and a needle that is movably disposed within the guide tube; another aspect of such a system utilizes an expandable element, at least one fluid delivery tube or ablation conduit that is fixed, secured, or otherwise anchored to the expandable element, and at least one injector that extends from an outer perimeter of the corresponding fluid delivery tube, is fluidly interconnected with the corresponding fluid delivery tube, and protrudes beyond an outer perimeter of the expandable element at least when in its deployed state or configuration, and yet another aspect of such a system includes an inflatable tube, where at least one injector is separately attached to the inflatable tube and is fluidly connected with an interior space of the inflatable tube.

Various aspects of the present disclosure are also addressed by the following paragraphs and in the noted combinations:

1. A chemical ablation therapy delivery system, comprising:
an expandable element;
a guide tube attached to said expandable element; and
a needle movably disposed within said guide tube.
2. The system of paragraph 1, wherein said guide tube is attached to said expandable element such that at least part of said guide tube is always maintained in a fixed position relative to said expandable element.
3. The system of any of paragraphs 1-2, wherein said guide tube extends within an interior of said expandable element.
4. The system of paragraph 3, wherein said guide tube extends from said interior toward a perimeter wall of said expandable element and is attached to said perimeter wall of said expandable element.
5. The system of any of paragraphs 1-2, wherein said guide tube is disposed entirely exteriorly of said expandable element.
6. The system of any of paragraphs 1, 2, and 5, wherein said guide tube extends along an exterior of said expandable element.
7. The system of any of paragraphs 1-6, wherein said expandable element is selected from the group consisting of a balloon and a stent.
8. The system of any of paragraphs 1-2, wherein said expandable element comprises a first expandable element and a second expandable element, wherein said second expandable element is disposed about said first expandable element, and wherein said guide tube is disposed between said first expandable element and said second expandable element and is attached to said second expandable element.
9. The system of paragraph 8, wherein said first expandable element and said second expandable element are each in the form of a balloon.
10. The system of any of paragraphs 1-2, wherein said expandable element is in the form of an inflatable tube comprising a first end, a second end spaced from said first end, an outer sidewall that extends between said first end and said second end, and an inner sidewall that extends between said first end and said second end.
11. The system of paragraph 10, wherein said inflatable tube proceeds along an arcuate path from said first end to said second end when said inflatable tube is in a
12. The system of paragraph 11, said outer sidewall and said inner sidewall of said inflatable tube are disposed about a center axis when said inflatable tube is in said deployed configuration, and wherein said first end and said second end are radially spaced from one another, relative to and about said center axis.
13. The system of any of paragraphs 10-12, wherein said guide tube extends along an exterior of said outer sidewall of said inflatable tube.
14. The system of any of paragraphs 1-13, wherein said needle is movable relative to said guide tube between a delivery position and a deployed position, and wherein said needle is entirely retained within said guide tube when in said delivery position and extends beyond said guide tube when in said deployed position.
15. The system of any of paragraphs 1-14, further comprising an ablation source interconnected with said needle.
16. The system of paragraph 15, wherein said ablation source comprises at least one ablation agent.
17. The system of any of paragraphs 1-16, further comprising a plurality of said guide tubes and a corresponding plurality of said needles, wherein each said guide tube has a corresponding said needle.
18. The system of paragraph 17, wherein each of said plurality of guide tubes comprises an exit and said expandable element comprises a central axis that corresponds with a length dimension of said expandable element.
19. The system of paragraph 18, wherein said exit of at least some of said plurality of guide tubes are disposed at different radial positions relative to and about said central axis of said expandable element.
20. The system of any of paragraphs 18-19, wherein said exit of at least some of said plurality of guide tubes are disposed at different positions along a length of said expandable element.
21. A chemical ablation therapy delivery system, comprising:
an expandable element; and
a fluid delivery tube fixed to said expandable element; and
an injector that extends from an outer perimeter of said fluid delivery tube, is at least fluidly connectable with an interior of said fluid delivery tube, and protrudes beyond an outer perimeter of said expandable element.
22. The system of paragraph 21, wherein said fluid delivery tube is disposed on an exterior surface of said expandable element.
23. The system of paragraph 21, wherein said fluid delivery tube is disposed on an interior surface of said expandable element.
24. The system of any of paragraph 21-23, wherein said fluid delivery tube comprises at least one material so as to be at least one of flexible, elastic, expandable, and deformable.

25. The system of any of paragraphs 21-24, wherein said injector comprises a spike which in turn comprises at least one discharge port.
26. The system of any of paragraphs 21-25, further comprising a plurality of said injectors spaced along a length of said fluid delivery tube.
27. The system of any of paragraphs 21-25, further comprising an ablation source interconnected with said fluidly delivery tube.
28. The system of paragraph 27, wherein said ablation source comprises at least one ablation agent.
29. The system of any of paragraphs 21-28, further comprising a plurality of said fluid delivery tubes.
30. The system of paragraph 29, wherein said expandable element comprises a central axis that corresponds with a length dimension of said expandable element.
31. The system of paragraph 30, wherein at least one said injector of at least some of said plurality of fluid delivery tubes are disposed at different radial positions relative to and about said central axis of said expandable element.
32. The system of any of paragraphs 30-31, wherein at least one said injector of at least some of said plurality of fluid delivery tubes are disposed at different positions along a length of said expandable element.
33. The system of any of paragraphs 21-32, wherein said expandable element is selected from the group consisting of a balloon and a stent.
34. A chemical ablation therapy delivery system, comprising:

an inflatable tube comprising a first end, a second end spaced from said first end, an outer sidewall that extends between said first end and said second end, and an inner sidewall that extends between said first end and said second end;

an injector separately attached to said inflatable tube, wherein said injector is at least fluidly connectable with an interior space of said inflatable tube.

35. The system of paragraph 34, wherein said inflatable tube proceeds along an arcuate path from said first end to said second end when said inflatable tube is in a
36. The system of paragraph 35, wherein said outer sidewall and said inner sidewall are disposed about a center axis when said inflatable tube is in said deployed configuration, and wherein said first end and said second end are radially spaced from one another, relative to and about said center axis.
37. The system of any of paragraphs 34-36, wherein said injector comprises at least one discharge port.
38. The system of any of paragraphs 34-36, wherein said injector comprises a spike, which in turn comprises at least one discharge port.
39. The system of any of paragraphs 34-38, further comprising a plurality of said injectors spaced along a length of said outer sidewall.
40. The system of any of paragraphs 34-39, further comprising an ablation source interconnected with said inflatable tube.
41. The system of paragraph 40, wherein said ablation source comprises at least one ablation agent.

DETAILED DESCRIPTION

Figure 1:
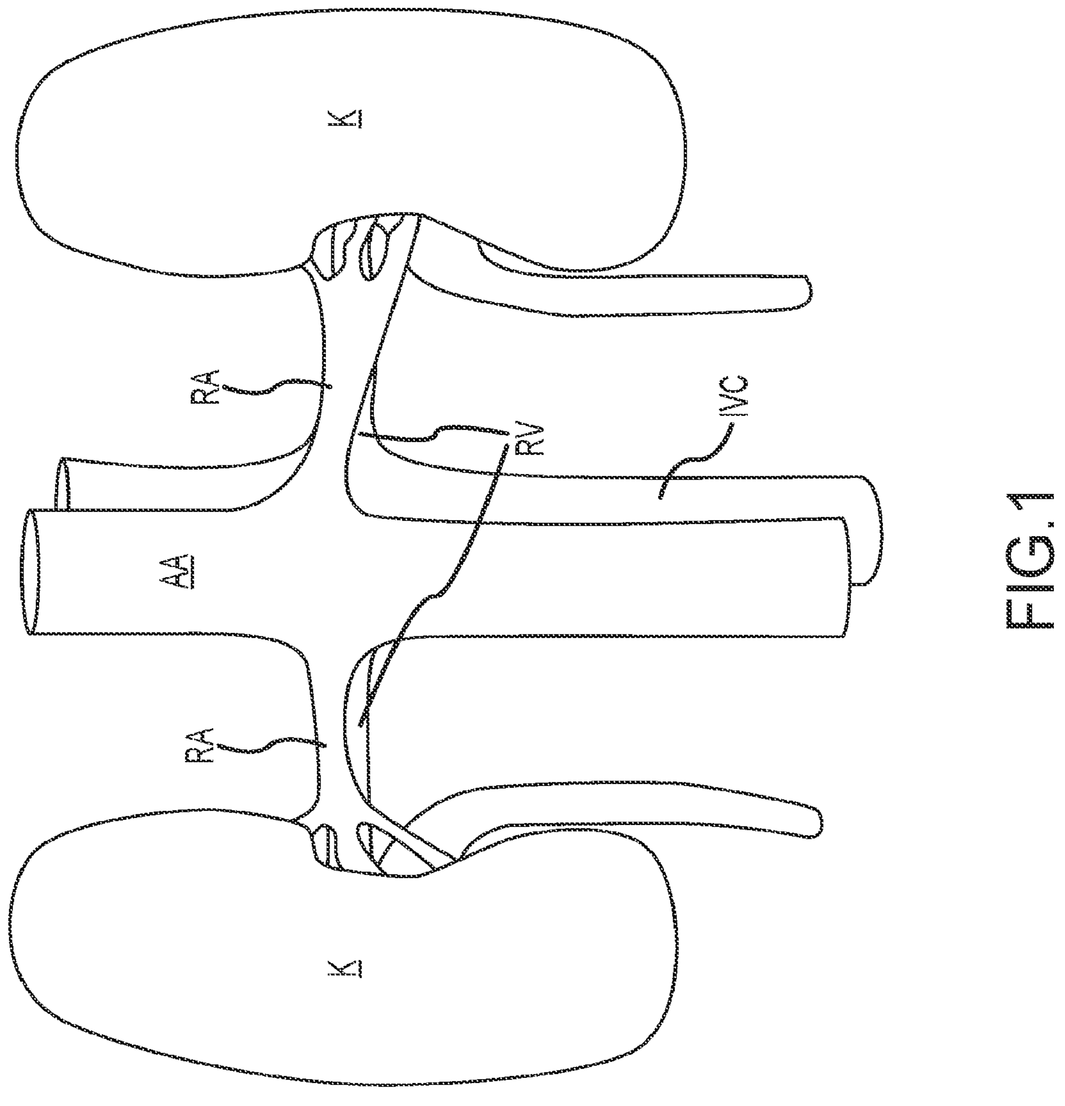
FIG. 1 is a schematic of a human renal anatomy.

One application for the various chemical ablation therapy delivery systems disclosed herein is denervation, including denervating renal nerves. A human renal anatomy is presented in FIG. 1 and includes kidneys K that are supplied with oxygenated blood by renal arteries RA. The kidneys K are connected to the heart by the abdominal aorta AA. Deoxygenated blood flows from the kidneys K to the heart via renal veins RV and the inferior vena cava IVC. Nerves are disposed about the main renal artery, as well as its various branches that extend from the main renal artery to the corresponding kidney K. Additional applications for the various ablation elements and/or ablation systems disclosed herein include tumor ablation, tissue ablation, and the like.

Figure 2:
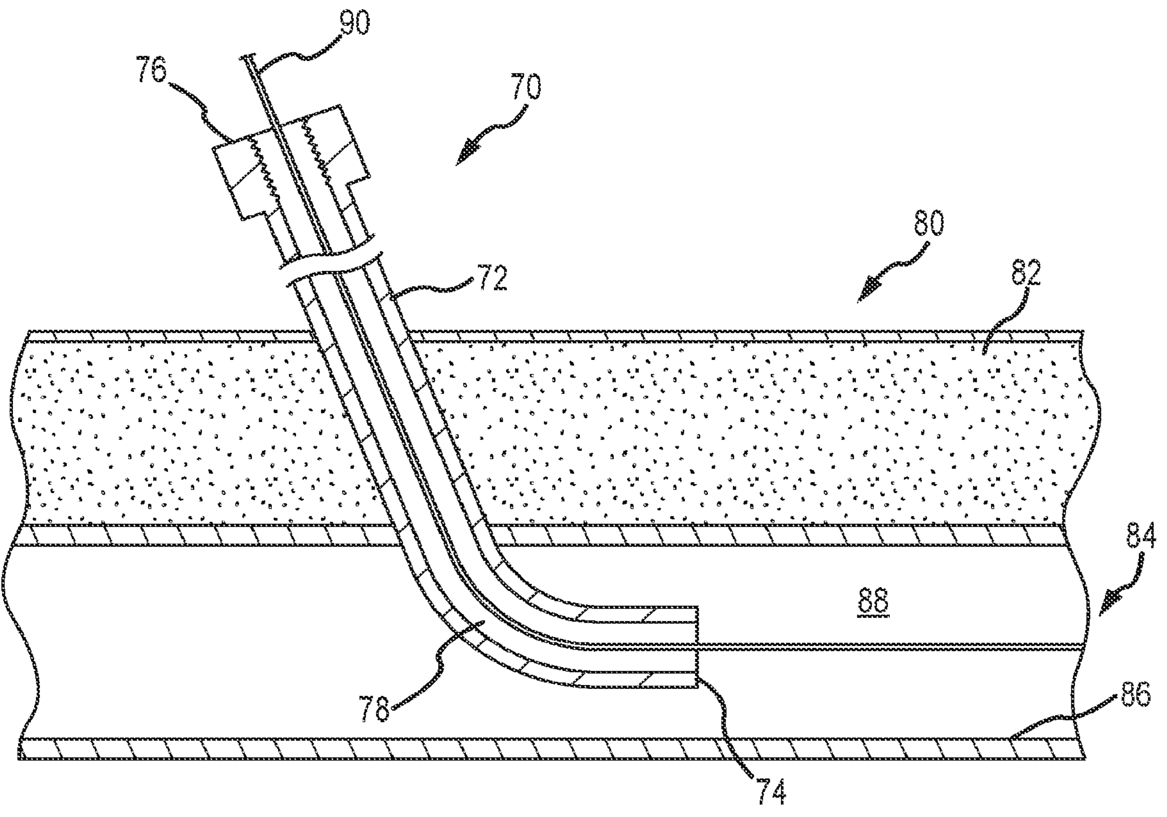
FIG. 2 is a cross-sectional schematic of a representative guide catheter assembly deployed within a patient's vasculature and that may be used to deliver one or more of the ablation catheters disclosed herein to a target location.

A guide catheter may be used in relation to one or more of the chemical ablation therapy delivery systems addressed herein, a representative one of which is illustrated in FIG. 2 and that is identified by reference numeral 70. The guide catheter 70 includes a generally tubular guide shaft 72, which in turn includes a distal end 74, a proximal end 76, and a guide lumen 78 that extends through guide shaft 72 (extending between the distal end 74 and the proximal end 76). The guide catheter 70 is shown as having been directed through tissue 82 of a patient 80, through a wall 86 of a representative vessel 84, and into the lumen 88 of the vessel 84. A guide wire 90 extends through the guide catheter 70 and into the lumen 88 of the vessel 84. As is known in the art: 1) a needle, a short guide wire, and a dilator (removably disposed in the guide lumen 78 of the guide catheter 70 may be used to introduce the guide catheter 70 into the lumen 88 of the vessel 84 (e.g., U.S. Pat. No. 10,271,873); and 2) the guide wire 90 and guide catheter 70 may be advanced along the vessel 84 to the target location, for instance for releasing one or ablation elements at the target location.

Figure 3:
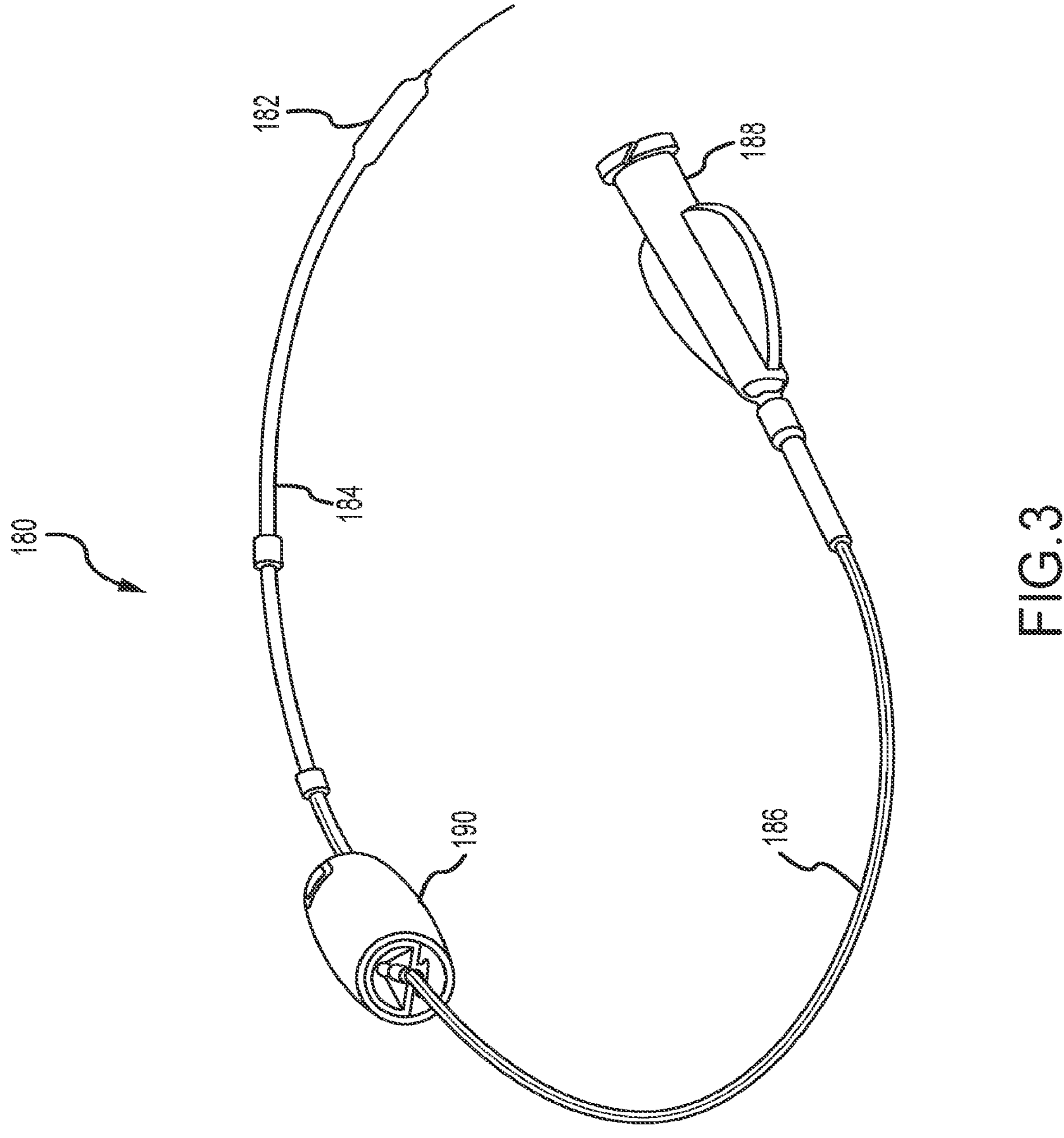
FIG. 3 is representative balloon catheter that may be utilized by/adapted for various of the ablation systems disclosed herein.

A representative catheter that may be utilized by/adapted for one or more of the chemical ablation therapy delivery systems addressed herein is illustrated in FIG. 3 and is identified by reference numeral 180. The catheter 180 includes a balloon 182 (more generally, an expandable element), a distal shaft 184, a proximal shaft 186, a fitting 188, and a guide member 190. The fitting 188 may be configured to accommodate receipt of separate flows from two different feed sources (e.g., an ablation agent; an inflation medium). A portion of each of feed may extend from the fitting 188, through the proximal shaft 186, through the distal shaft 184, and to the balloon 182.

Figure 3A:
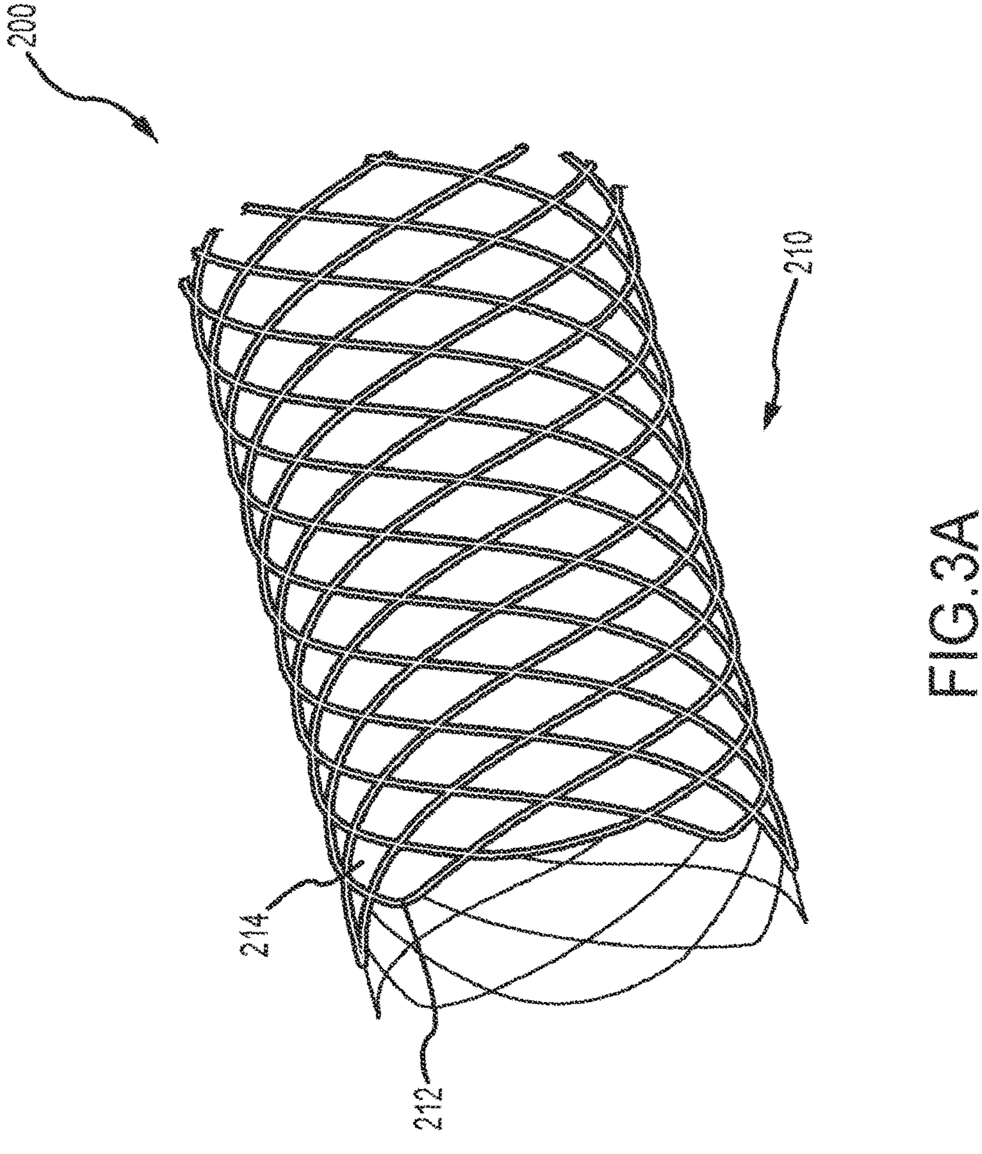
FIG. 3A is a perspective view of a representative expandable stent that may be utilized by various of the ablation systems disclosed herein.

FIG. 3A is a perspective view of representative stent 200 (e.g., more generally in expandable element) that may be utilized by one or more of the chemical ablation therapy delivery systems addressed herein. The stent 200 utilizes an expandable skeleton or skeletal structure 212 (e.g., Nitinol), and includes a sidewall or perimeter wall 210 that may be of any appropriate configuration (e.g., cylindrical). The skeleton 212 may be of any appropriate pattern/configuration, and will typically include various openings 214 that are distributed throughout the skeleton 212 and that may be of any appropriate size and/or configuration. When the stent 200 is delivered to a target location within a vessel of the patient (e.g., using the guide catheter 70 of FIG. 3; with the stent 200 replacing the balloon 182 in the FIG. 3 configuration), the stent 200 may be advanced beyond the distal end of a guide catheter (e.g., distal end 74 of guide catheter 70 of FIG. 3) and the stent 200 (via its material properties) will expand to dispose the sidewall 210 of the stent 200 in contact with the inner wall of the vessel.

Various embodiments of chemical ablation therapy delivery systems will now be described. Each of the various embodiments of such systems accommodate delivery of a more controlled volume of one or more ablation agents to one or more extravascular target locations within the body of a patient.

Figure 4A:
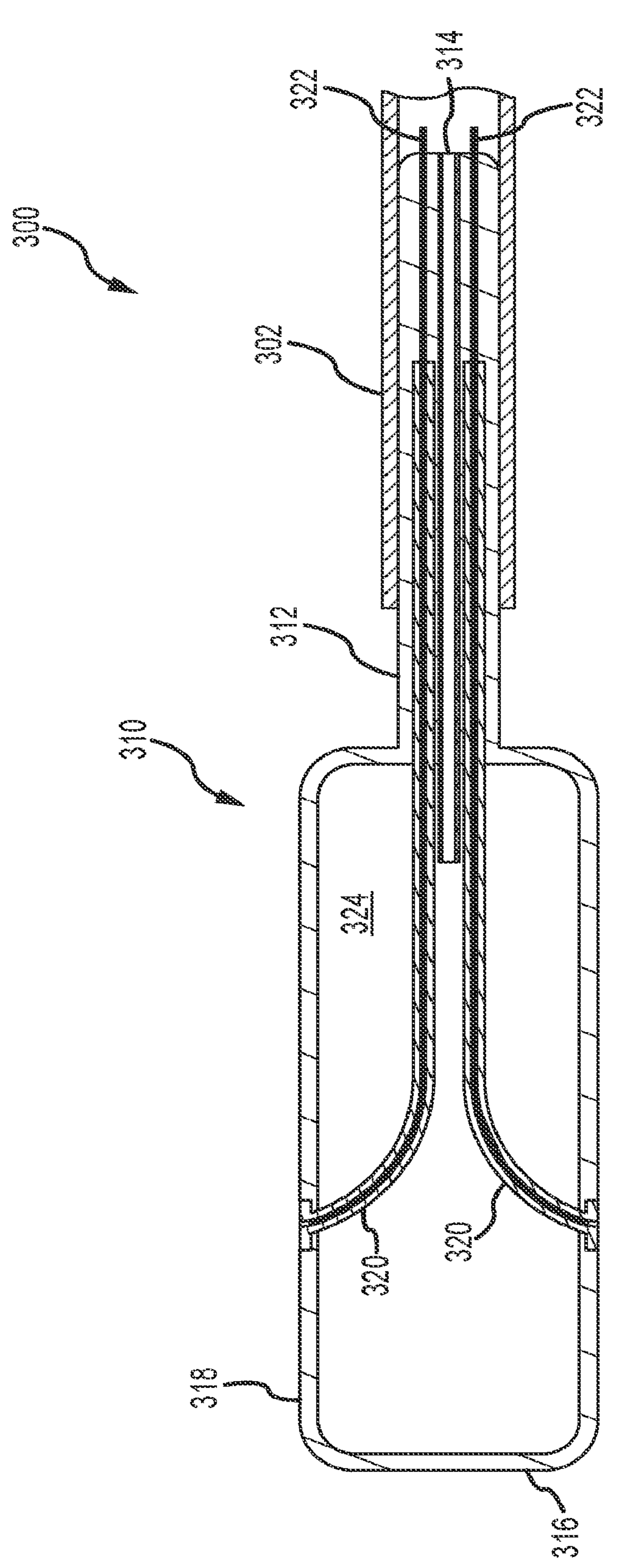
FIG. 4A is a cross-sectional schematic of a chemical ablation therapy delivery system that utilizes guide tubes that extend within and that are attached to an expandable element, and through which an ablation agent needle may be deployed.
Figure 4B:
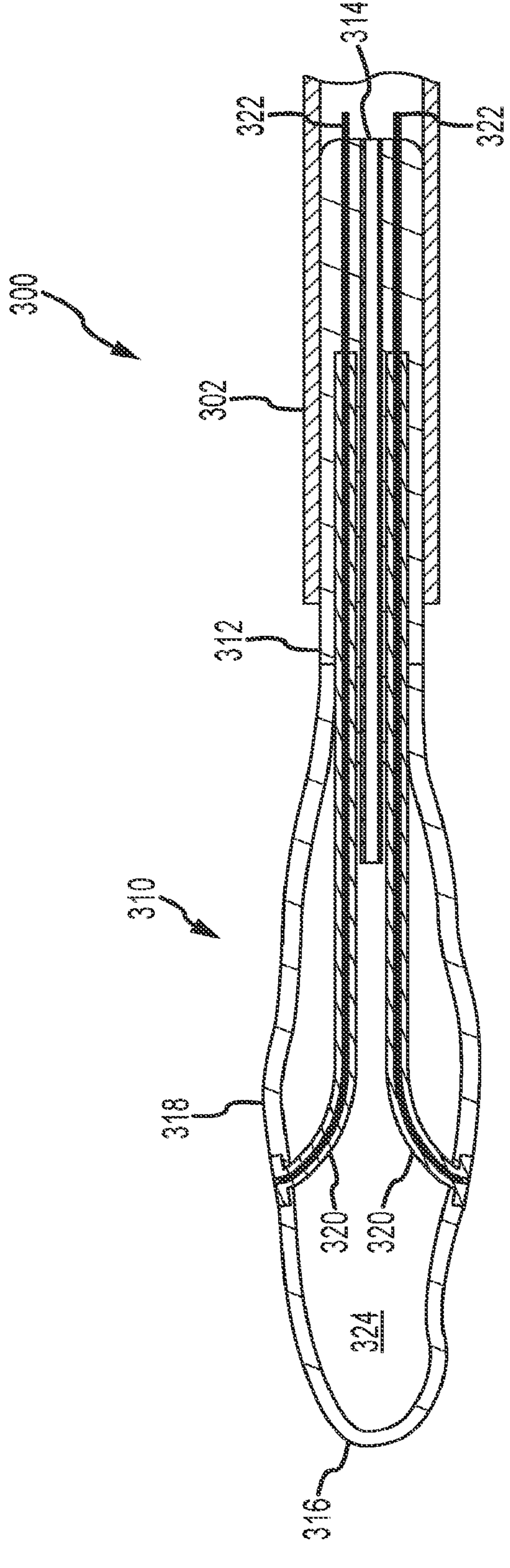
FIG. 4B is a cross-sectional schematic of an embodiment of the chemical ablation therapy delivery system of FIG. 4B, but in an at least partially deflated configuration.

A schematic of an embodiment of a chemical ablation therapy delivery system is illustrated in FIGS. 4A-4B and is identified by reference numeral 300. This delivery system 300 may be characterized as including/utilizing a guide catheter 302 (e.g., guide catheter 70 of FIG. 2) and what may be characterized as an ablation catheter 310. Generally, the guide catheter 302 may be utilized to deliver the ablation catheter 310 to a target location within a vessel of a patient, typically with the ablation catheter 310 being in a delivery state or configuration (e.g., deflated; contracted) and with the ablation catheter 310 being retained within the guide catheter 302. It should be appreciated that the catheter 180 of FIG. 3 may be adapted in accord with the ablation catheter 310 of FIGS. 4A-4B.

The ablation catheter 310 includes a distal shaft 312 (e.g., in accord with the distal shaft 184 of the catheter 180 shown in FIG. 3) that is movable relative to the guide catheter 302 along its length dimension. An expandable element 316 (e.g., a balloon or a stent) is appropriately mounted to the distal shaft 312 (only schematically shown in the various figures), and includes what may be characterized as a sidewall 318. The distal shaft 312 is advanced relative to the guide catheter 302 to dispose the expandable element 316 of the ablation catheter 310 beyond a distal end of the guide catheter 302. In the case where the expandable element 316 is in the form of a stent (e.g., stent 200 of FIG. 3A), this repositioning of the expandable element 316 relative to the guide catheter 302 itself may dispose the ablation element 316 in its deployed state or configuration (e.g., expanded; the stent may be formed from a material that will expand the stent when disposed beyond the distal end of the guide catheter 302, and where the sidewall of the stent will then be disposed in interfacing relation with a corresponding portion of an inner wall that defines a vessel in which the ablation catheter 310 is disposed). In the case where the expandable element 316 is in the form of a balloon, the ablation catheter 310 includes an inflation tube 314 to direct an appropriate inflation medium into the expandable element 316 to dispose its sidewall 318 into interfacing relation with a corresponding portion of an inner wall that defines a vessel in which the ablation catheter 310 is disposed (an expanded or deployed state or configuration).

The ablation catheter 310 includes one or more guide tubes 320, with each guide tube 320 having an ablation needle 322 disposed therein and that is movable relative to the corresponding guide tube 320 along its length dimension. Each needle 322 is fluidly connected with an appropriate ablation agent source (e.g., ablation agent source 152 in FIG. 9, discussed below). Any appropriate number of guide tubes 320 may be utilized, and any appropriate spacing may be utilized between each adjacent pair of guide tubes 320. Each guide tube 320 may be of any appropriate length and may be attached to the expandable element 316 at any appropriate location. Each guide tube 320 and its corresponding needle 322 may be formed from a material or combination of materials so as to be at least one of flexible, elastic, expandable, and deformable. This allows each guide tube 320 and its corresponding needle 322 to change shape as the expandable element 316 moves from its delivery state or configuration to its deployed state or configuration (e.g., via the material properties of the guide tubes 320 and needles 322). Moving the expandable element 316 from its delivery state or configuration to its deployed state or configuration causes a corresponding movement of the guide tubes 320 and the needles 322. Representative materials for the guide tubes 320 include without limitation plastic (e.g., Pebax®, polypropylene, nylon, etc.). Representative materials for the needles 322 include without limitation nitinol or stainless steel. The inflation tube 314, as well as each guide tube 320 and its corresponding needle 322, may be disposed in/extend through the distal shaft 312.

Each guide tube 320 extends within an interior 324 of the expandable element 316. Moreover, each guide tube 320 is appropriately attached (e.g., fixed, secured, or otherwise anchored) to the expandable element 316, typically its sidewall 318 (e.g., such that at least part of each guide tube 320 is at all times maintained in a stationary or fixed position relative to the expandable element 316). In the case where the expandable element 316 is in the form of a balloon, each guide tube 320 could extend completely through the balloon and with a seal being provided between the balloon and each such guide tube 320. In the case where the expandable element 316 is in the form of a stent, each guide tube 320 may be positioned within an opening of the stent (e.g., opening 214 of the stent 200 of FIG. 3A) and may be appropriately secured or fixed to the skeleton of the stent (e.g. skeleton 212 of the stent 200 of FIG. 3A).

When the ablation catheter 310 is in its delivery configuration (disposed within the guide catheter 302), each guide tube 320 and its corresponding needle 322 may be at least generally axially extending. FIG. 4B illustrates the ablation catheter 310 having been positioned beyond the free end of the guide catheter 302, and with the expandable element 316 being in the form of a balloon and in an intermediate state—between its delivery configuration and its deployed configuration. When the expandable element 316 is in its fully deployed state or configuration (e.g., FIG. 4A), the sidewall 318 of the expandable element 316 should be disposed in interfacing relation with a corresponding portion of an inner wall that defines a vessel in which the ablation catheter 310 is disposed. At this time each needle 322 may be maintained in a retracted state relative to its corresponding guide tube 320. Thereafter, each needle 322 may be advanced relative to its corresponding guide tube 320 such that each needle 322 is disposed beyond a distal end of the guide tube 320 and is advanced through the inner wall that defines a vessel in which the ablation catheter 310 is disposed. With each needle 322 now being in a deployed position (the distal tip of each needle 322 being disposed outside of the vessel), an ablation agent or combination of ablation agents may be directed through each needle 322 to provide for an extravascular chemical ablation.

Figure 4C:
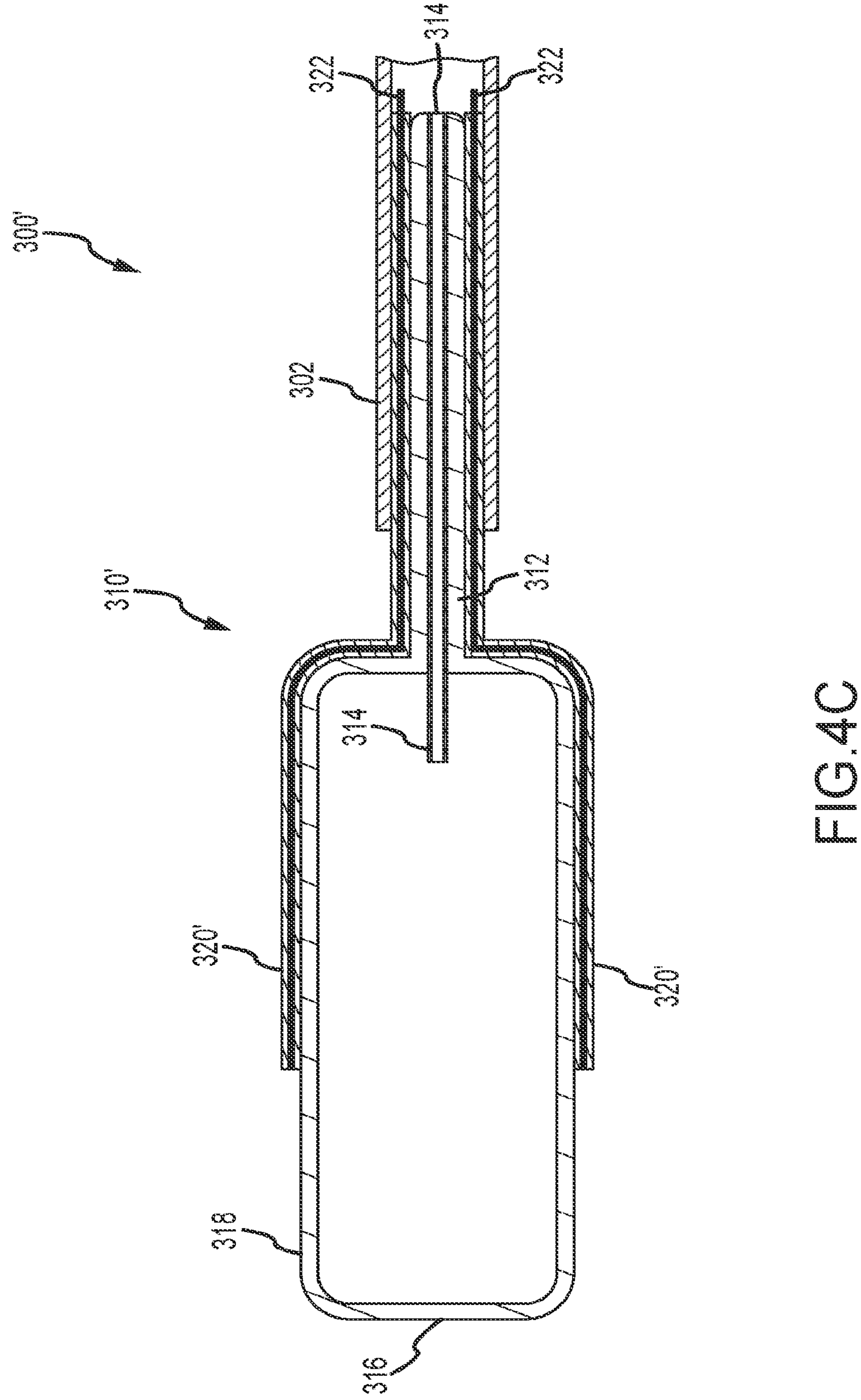
FIG. 4C is a cross-sectional schematic of a variation of the chemical ablation therapy delivery system of FIG. 4A, where the guide tubes are disposed on an exterior of the expandable element, and through which an ablation agent needle may be deployed.

A schematic of a variation of the chemical ablation therapy delivery system 300 of FIGS. 4A-4B is presented in FIG. 4C and is identified by reference numeral 300'. Corresponding components of the system 300 (FIGS. 4A-4B) and the system 300' (FIG. 4C) are identified by a common reference numeral and unless otherwise noted herein to the contrary, the foregoing discussion of these corresponding components remains applicable to the system 300' of FIG. 4C. Those corresponding components that differ in at least some respect are identified by a "single prime" designation in the case of the chemical ablation therapy delivery system 300' of FIG. 4C. The primary difference between the system 300 of FIGS. 4A-4B and the system 300' of FIG. 4C is that the guide tubes 320 for the ablation catheter 310' of FIG. 4C are entirely disposed exteriorly of the expandable element 316. For instance, each guide tube 320 may extend along an outer surface of the sidewall 318 of the expandable element 316, with each guide tube 320 still being appropriately attached to the expandable element 316.

Figure 4D:
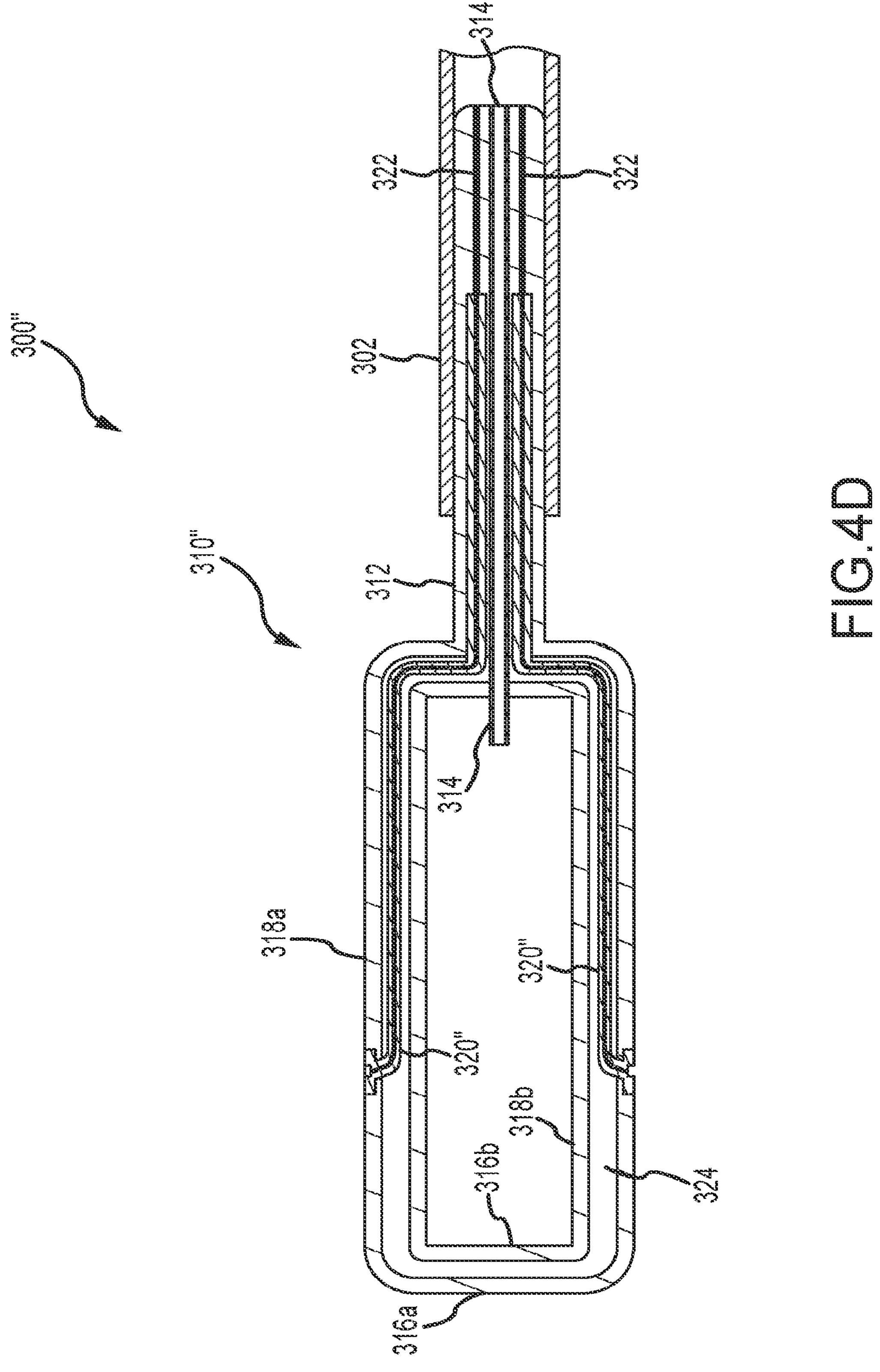
FIG. 4D is a cross-sectional schematic of a variation of the chemical ablation therapy delivery system of FIG. 4A, where the system utilizes inner and outer balloons and with guide tubes being disposed between these inner and outer balloons and through which an ablation agent needle may be deployed.

A schematic of a variation of the chemical ablation therapy delivery system 300 of FIGS. 4A-4B is presented in FIG. 4D and is identified by reference numeral 300". Corresponding components of the system 300 (FIGS. 4A-4B) and the system 300" (FIG. 4D) are identified by a common reference numeral and unless otherwise noted herein to the contrary, the foregoing discussion of these corresponding components remains applicable to the system 300" of FIG. 4D. Those corresponding components that differ in at least some respect are identified by a "double prime" designation in the case of the chemical ablation therapy delivery system 300" of FIG. 4D. The primary difference between the system 300 of FIGS. 4A-4B and the system 300" of FIG. 4D is that the expandable element in the case of the ablation catheter 310" of FIG. 4D is in the form of an outer balloon **316*a* and an inner balloon 316*b*. Each guide tube 320 is disposed in the space 324 between the inner balloon 316*b* and the outer balloon 316*a* (e.g., between the sidewall 318*a* of the outer balloon 316*a* and the sidewall 318*b* of the inner balloon 316*b*). Each guide tube 320 is appropriately attached to the outer balloon 316*a*, typically its sidewall 318*a*. Each guide tube 320 may extend completely through the outer balloon 316*a* and with a seal being provided between the outer balloon 316*a* and each such guide tube 320**.

Figure 5A:
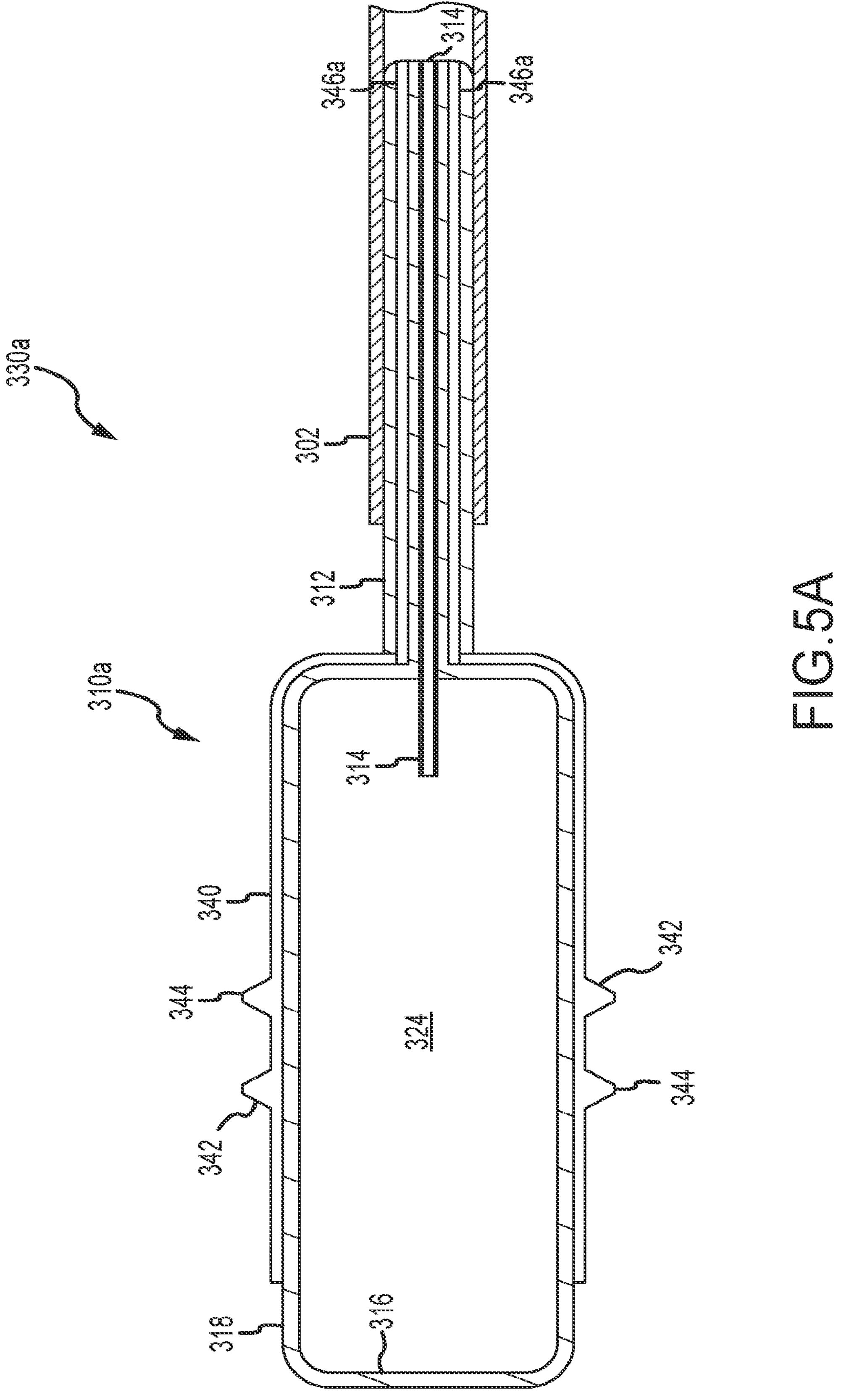
FIG. 5A is a cross-sectional schematic of a chemical ablation therapy delivery system that utilizes a plurality of ablation conduits disposed on an exterior surface of an expandable element, with each ablation conduit including a plurality of injection spikes.
Figure 5B:
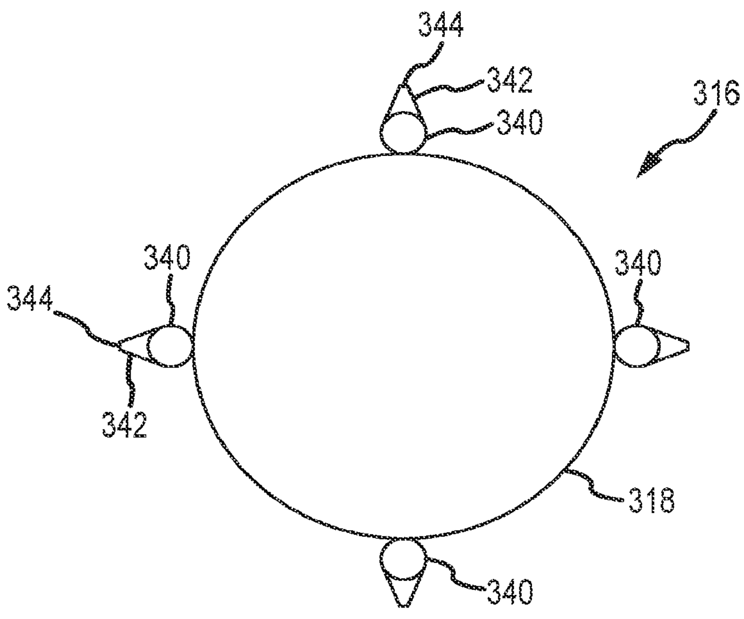
FIG. 5B is a cross-sectional view of the expandable element shown in FIG. 5A, taken along a length dimension of the expandable element.
Figure 5C:
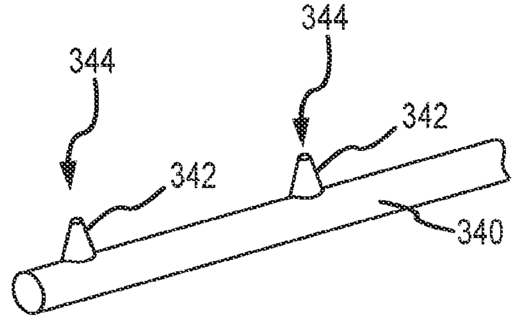
FIG. 5C is a perspective view of a portion of one of the ablation conduits used by the system of FIG. 5A.

A schematic of an embodiment of a chemical ablation therapy delivery system is illustrated in FIGS. 5A-5C and is identified by reference numeral **330*a*. Corresponding components of the system 300 (FIGS. 4A-4B) and the system 330*a* (FIGS. 5A-5C) are identified by a common reference numeral, and unless otherwise noted herein to the contrary the foregoing discussion of these corresponding components remains applicable to the system 330*a* of FIGS. 5A-5C. This delivery system 330*a* may be characterized as including/utilizing a guide catheter 302 (e.g., guide catheter 70 of FIG. 2) and what may be characterized as an ablation catheter 310*a*. Generally, the guide catheter 302 may be utilized to deliver the ablation catheter 310*a* to a target location within a vessel of a patient, typically with the ablation catheter 310*a* being in a delivery state or configuration (e.g., deflated; contracted) and with the ablation catheter 310 being retained within the guide catheter 302. It should be appreciated that the catheter 180 of FIG. 3 may be adapted in accord with the ablation catheter 310*a* of FIGS. 5A-5**C.

The ablation catheter **310*a* includes a distal shaft 312 (e.g., in accord with the distal shaft 184 of the catheter 180 shown in FIG. 3) that is movable relative to the guide catheter 302 along its length dimension. An expandable element 316 (e.g., a balloon or a stent) is appropriately mounted to the distal shaft 312, and includes what may be characterized as a sidewall 318. The distal shaft 312 is advanced relative to the guide catheter 302 to dispose the expandable element 316 of the ablation catheter 310*a* beyond an end of the guide catheter 302. In the case where the expandable element 316 is in the form of a stent (e.g., stent 200 of FIG. 3A), this repositioning of the expandable element 316 relative to the guide catheter 302 itself may dispose the ablation element 316 in its deployed state or configuration (e.g., expanded; the stent may be formed from a material that will expand the stent when disposed beyond the distal end of the guide catheter 302, and where the sidewall of the stent will then be disposed in interfacing relation with a corresponding portion of an inner wall that defines a vessel in which the ablation catheter 310*a* is disposed). In the case where the expandable element 316 is in the form of a balloon, the ablation catheter 310***a* includes an inflation tube 314 to direct an appropriate inflation medium into the expandable element 316 to dispose its sidewall 318 into interfacing relation with a corresponding portion of an inner wall that defines a vessel in which the ablation catheter 310*a* is disposed (an expanded or deployed state or configuration).

The ablation catheter 310*a* includes one or more fluid delivery tubes/conduits or ablation tubes/conduits 340 that are fluidly connected with one or more ablation agent feed lines 346*a* that are disposed within/extend along the distal shaft 312 of the ablation catheter 310*a*. Each ablation agent feed line 346*a* is fluidly connected with an appropriate ablation agent source (e.g., ablation agent source 152 in FIG. 9, discussed below). Any appropriate number of ablation conduits 340 may be utilized, and any appropriate spacing may be utilized between each adjacent pair of ablation conduits 340 (e.g., four equally-spaced ablation conduits 340 being shown in FIG. 5B). Each ablation conduit 340 may be of any appropriate length and may be attached to the expandable element 316 at any appropriate location or combination of locations. Each ablation conduit 340 may be formed from a material or combination of materials so as to be at least one of flexible, elastic, expandable, and deformable. Representative materials for the ablation conduits 340 include without limitation nitinol, stainless steel, or composite.

Each ablation conduit 340 is disposed on an outer perimeter of the expandable element 316, including where one or more of the ablation conduits 340 extend along an outer surface of the sidewall 318 of the expandable element 316. Each ablation conduit 340 is appropriately attached (e.g., fixed, secured or otherwise anchored) to the expandable element 316, typically its sidewall 318. Moreover, each ablation conduit 340 includes one or more injectors or spikes 342, with each spike 342 including at least one discharge port 344. Any appropriate number of spikes 342 may be used by each ablation conduit 340, any appropriate spacing may be used between adjacent pairs of spikes 342 of a given ablation conduit 340, and any appropriate number of discharge ports 344 may be used by each spike 342. Any appropriate configuration may be used for the various spikes 342 to allow each spike 342 to pass through a wall of a vessel in which the ablation catheter 310*a* is positioned at a target location, and when the expandable element 316 is disposed in its deployed state or configuration (e.g., FIG. 5A).

When the ablation catheter 310*a* is in its delivery configuration (disposed within the guide catheter 302), each ablation conduit 340 for the ablation catheter 310*a* may be at least generally axially extending. When the expandable element 316 is in its fully deployed state or configuration (e.g., FIG. 5A), the sidewall 318 of the expandable element 316 should be disposed in interfacing relation with a corresponding portion of an inner wall that defines a vessel in which the ablation catheter 310*a* is disposed. Disposing the expandable element 316 in its deployed state or configuration should direct each spike 342 through the inner wall that defines a vessel in which the ablation catheter 310*a* is disposed. An ablation agent or combination of ablation agents may be directed through each spike 342 to provide for an extravascular chemical ablation at one or more targeted locations.

Figures 6A, 6B:
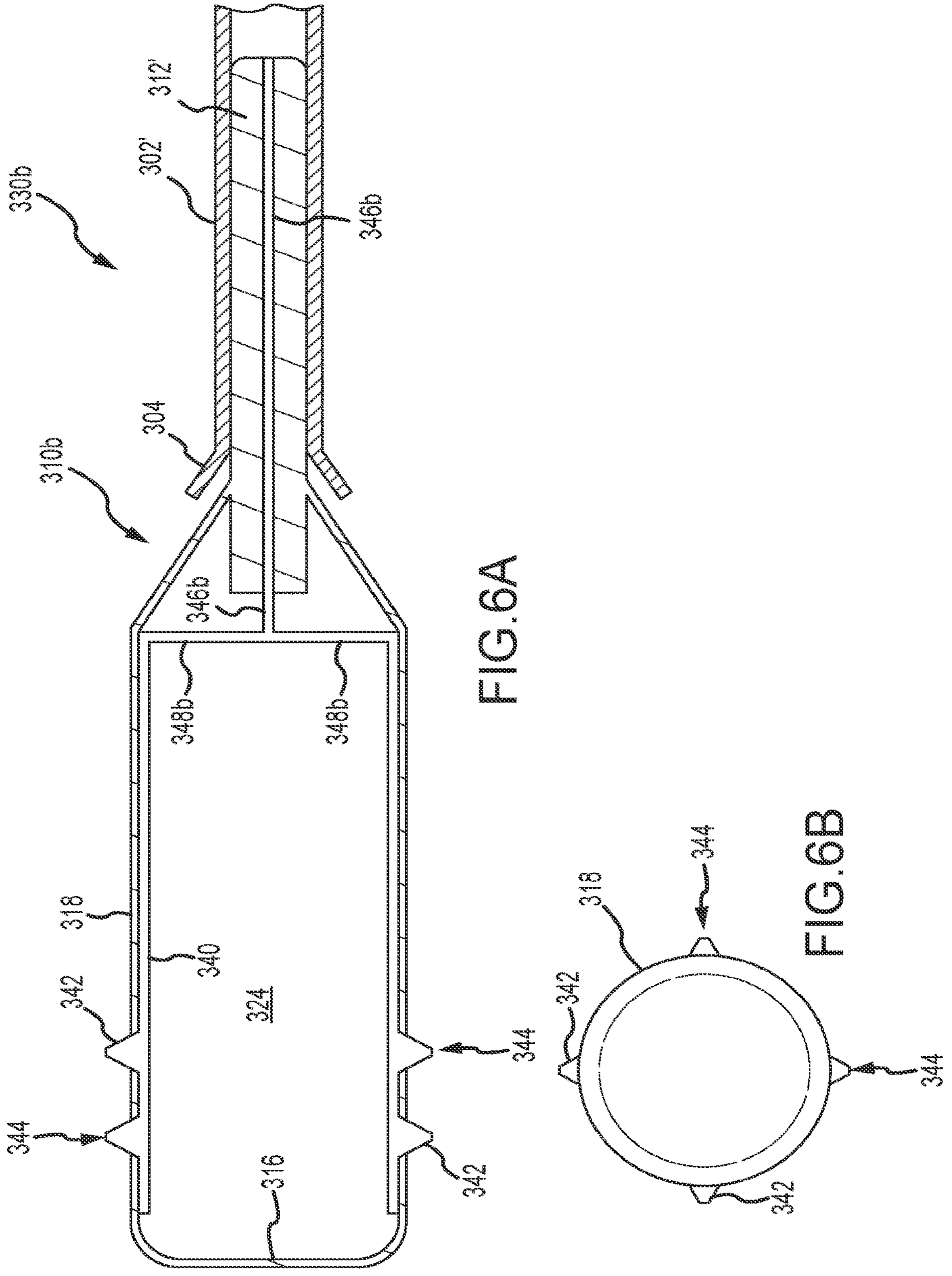
FIG. 6A is a cross-sectional schematic of a chemical ablation therapy delivery system that utilizes a plurality of ablation conduits disposed on an interior surface of an expandable element, with each ablation conduit including a plurality of injection spikes that extend through the expandable element.
FIG. 6B is a cross-sectional view of the expandable element shown in FIG. 6A, taken along a length dimension of the expandable element.

A schematic of a variation of the chemical ablation therapy delivery system 330*a* of FIGS. 5A-5C is presented in FIGS. 6A-6B and is identified by reference numeral 330*b*. Corresponding components of the system 330*a* (FIGS. 5A-5C) and the system 330*b* (FIGS. 6A-6B) are identified by a common reference numeral, and unless otherwise noted herein to the contrary the foregoing discussion of these corresponding components remains applicable to the system 330*b* of FIGS. 6A-6B. The primary difference between the system 330*a* of FIGS. 5A-5C and the system 330*b* of FIGS. 6A-6B is that the ablation conduits 340 for the ablation catheter 310*b* of FIGS. 6A-6B are disposed within the interior 324 of the expandable element 316. For instance, each ablation conduit 340 may extend along an inner surface of the sidewall 318 of the expandable element 316, with each ablation conduit 340 still being appropriately attached (e.g., fixed, secured or otherwise anchored) to the expandable element 316. In the case where the expandable element 316 is in the form of a balloon, each spike 342 may extend completely through the balloon and with a seal being provided between the balloon and each such spike 342. In the case where the expandable element 316 is in the form of a stent, each spike 342 may extend through an opening of the stent (e.g., opening 214 of the stent 200 of FIG. 3A) and may be appropriately attached to the skeleton of the stent (e.g., skeleton 212 of the stent 200 of FIG. 3A).

Additional differences exist between the system 330*a* of FIGS. 5A-5C and the system 330*b* of FIGS. 6A-6B. The system 330*b* utilizes a guide catheter 302' having a distal end section 304 that is flared (e.g., the inner diameter of the guide catheter 302' progressively increasing proceeding along the distal end section 304 and in the direction of a distal end of the guide catheter 302'). The guide catheter 302' may be used by any one or more of the various embodiments disclosed herein. The distal shaft 312' of the ablation catheter 310*b* has a single ablation agent feed line 346*b* that is fluidly connected with an appropriate ablation agent source (e.g., ablation agent source 152 in FIG. 9, discussed below). The ablation agent feed line 346*b* extends to one or more ablation agent distribution lines 348*b* that are disposed within the interior 324 of the ablation element 316. Each ablation conduit 340 is fluidly connected with at least one ablation agent distribution line 348*b*.

When the ablation catheter 310*b* is in its delivery state or configuration (disposed within the guide catheter 302'), each ablation conduit 340 for the ablation catheter 310*a* may be at least generally axially extending. When the expandable element 316 is in its fully deployed state or configuration (e.g., FIG. 6A), the sidewall 318 of the expandable element 316 should be disposed in interfacing relation with a corresponding portion of an inner wall that defines a vessel in which the ablation catheter 310*b* is disposed. Disposing the expandable element 316 in its deployed state or configuration should direct each spike 342 through the inner wall that defines a vessel in which the ablation catheter 310*b* is disposed. An ablation agent or combination of ablation agents may be directed through each spike 342 to provide for an extravascular chemical ablation at one or more targeted locations.

Figure 7:
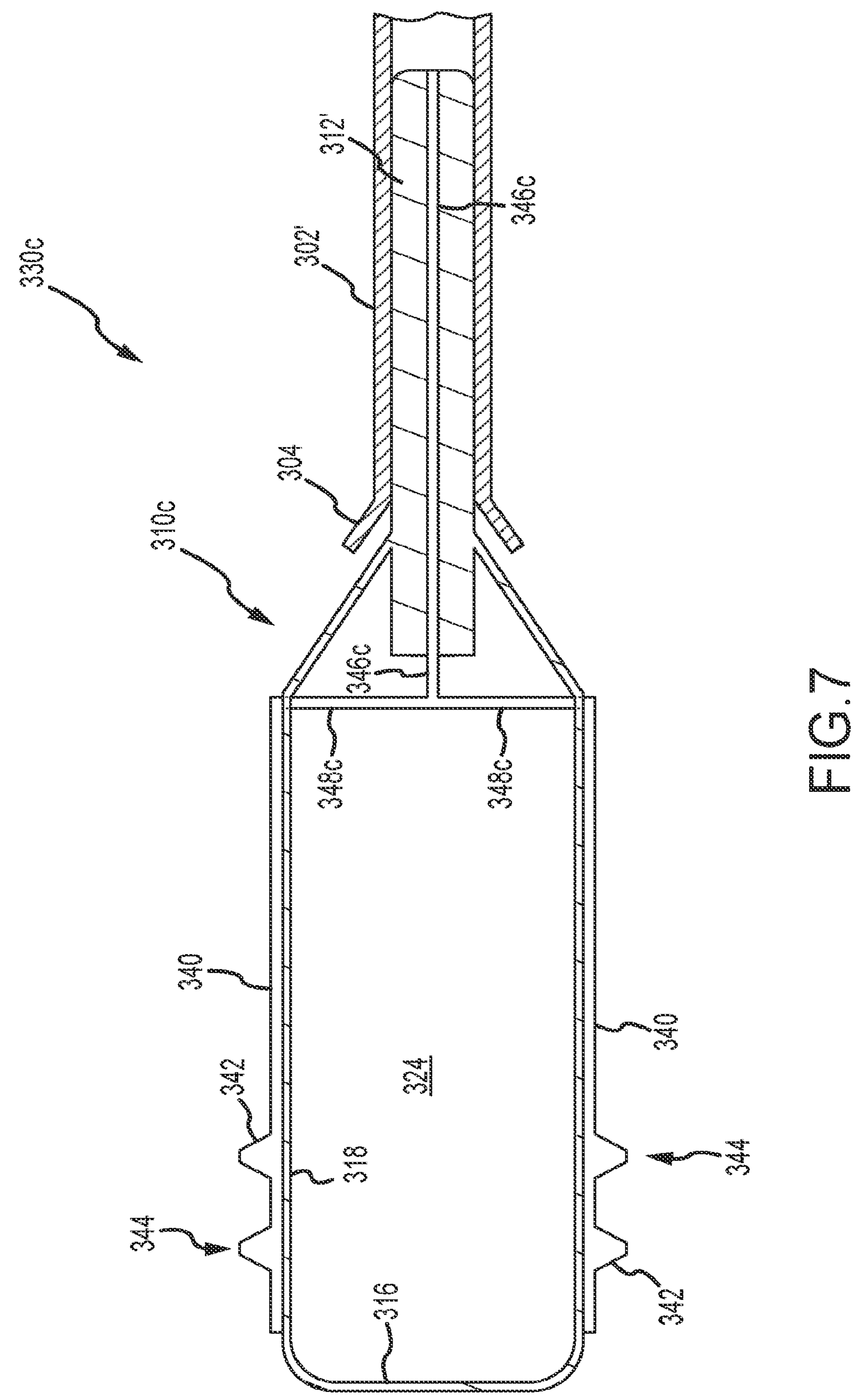
FIG. 7 is a cross-sectional schematic of a chemical ablation therapy delivery system that utilizes a plurality of ablation conduits disposed on an exterior surface of an expandable element, but with an alternative configuration for delivering an ablation agent compared to the configuration shown in FIG. 5A.

A schematic of a variation of the chemical ablation therapy delivery system 330*a* of FIGS. 5A-5C is presented in FIG. 7 and is identified by reference numeral 330*b*. Corresponding components of the system 330*a* (FIGS. 5A-5C) and the system 330*c* (FIG. 7) are identified by a common reference numeral, and unless otherwise noted herein to the contrary the foregoing discussion of these corresponding components remains applicable to the system 330*c* of FIG. 7. The primary difference between the system 330*a* of FIGS. 5A-5C and the system 330*c* of FIG. 7 is that the ablation catheter 310*c* of FIG. 7 uses an ablation agent feed line 346*c* and one or more ablation agent distribution lines 348*c* (e.g., at least generally in accord with the ablation catheter 310*b* of FIGS. 6A-6B). Each ablation agent distribution line 348*c* is disposed within the interior 324 of the ablation element 316. As the ablation conduits 340 are disposed on the outer surface of the expandable element 316 in the case of the ablation catheter 310*c*, each ablation agent distribution line 348*c* extends through the ablation element 316. In the case where the expandable element 316 is in the form of a balloon, each ablation agent distribution line 348*c* may extend completely through the balloon and with a seal being provided between the balloon and each such ablation agent distribution line 348*c*. In the case where the expandable element 316 is in the form of a stent, each ablation agent distribution line 348*c* may extend through an opening of the stent (e.g., opening 214 of the stent 200 of FIG. 3A) and may be appropriately secured or fixed to the skeleton of the stent (e.g. skeleton 212 of the stent 200 of FIG. 3A).

Figure 8A:
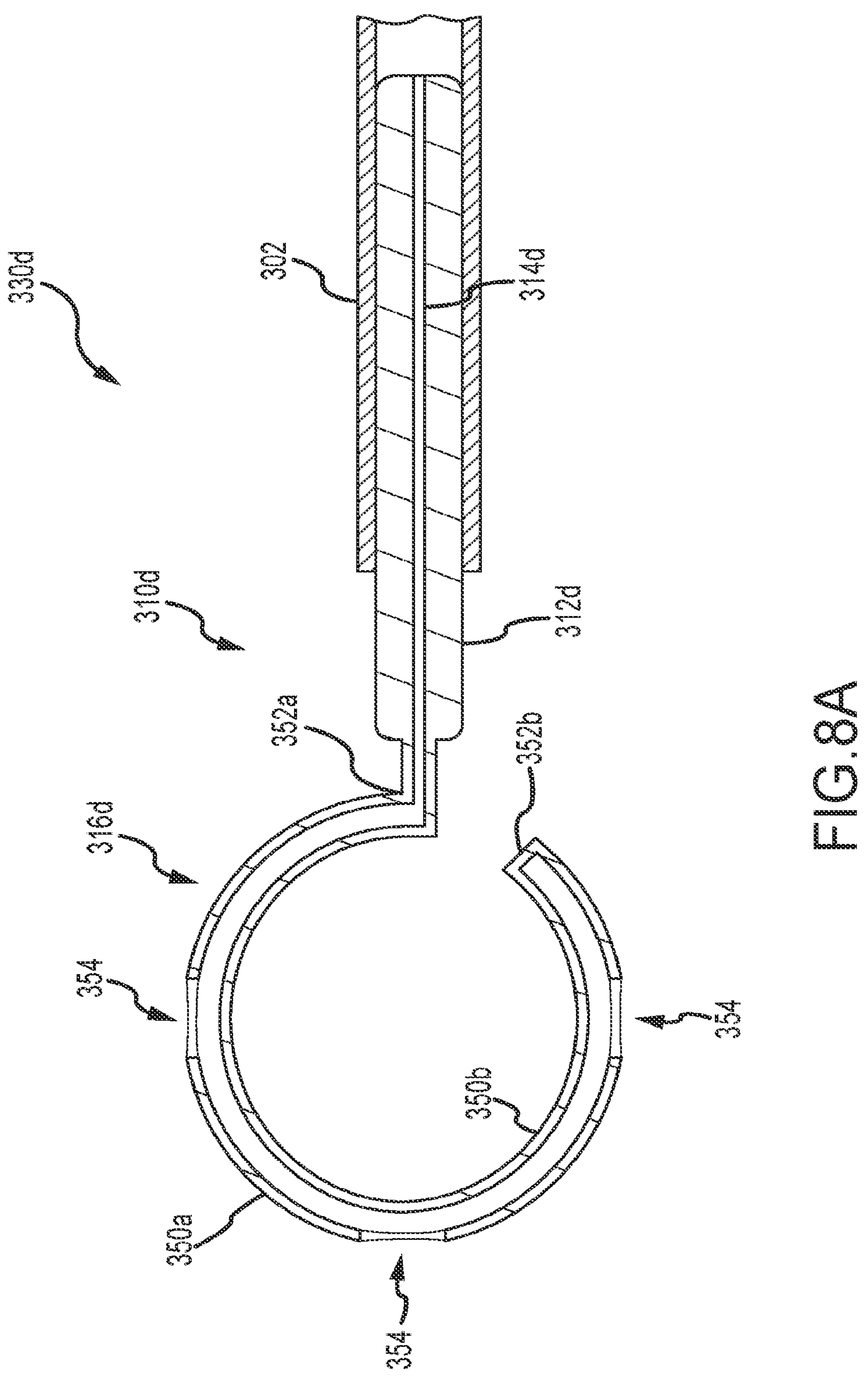
FIG. 8A is a cross-sectional schematic of a chemical ablation therapy delivery system that utilizes an inflatable tube with a plurality of injectors that are attached to the inflatable tube.
Figures 8B, 8C:
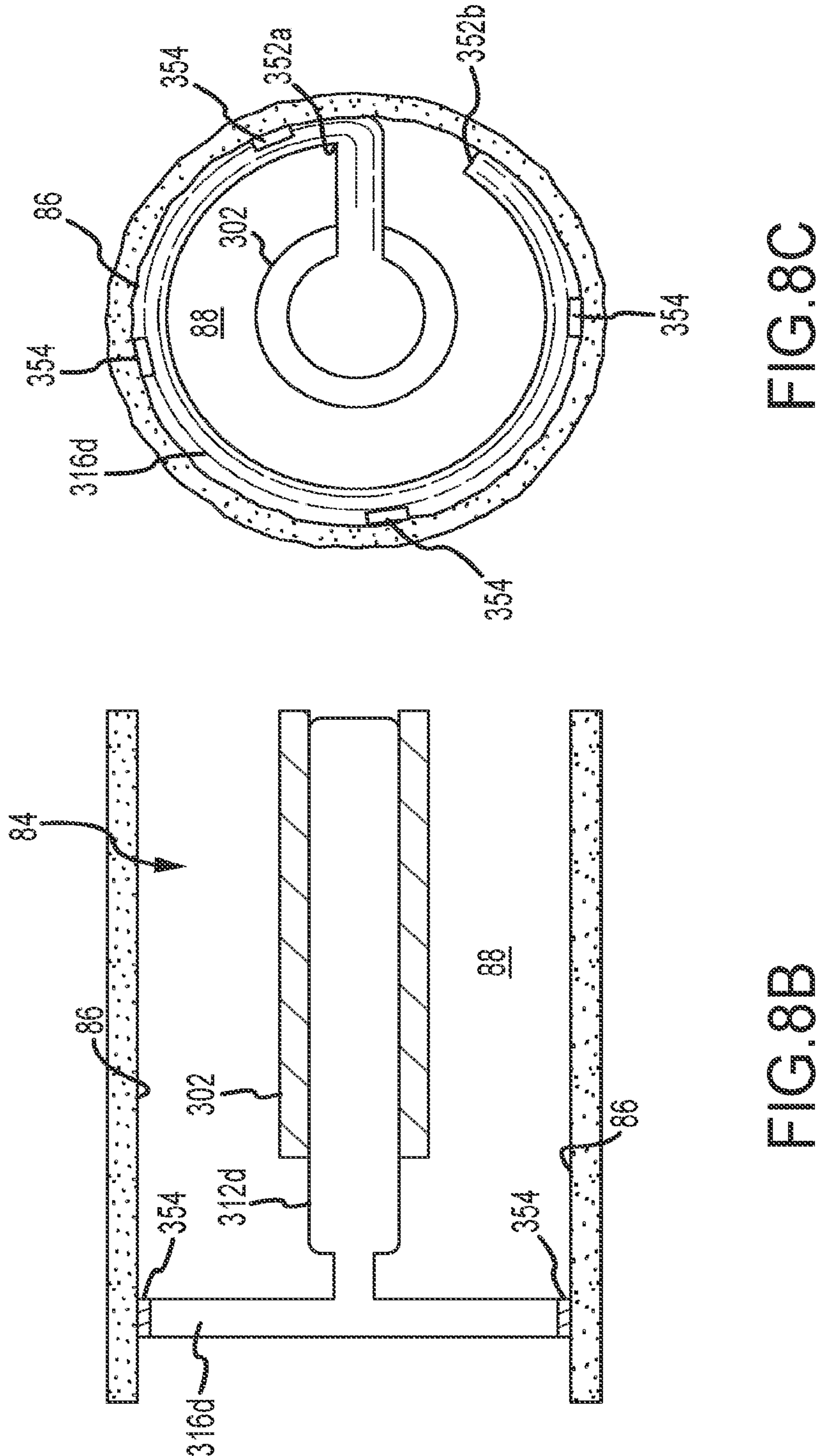
FIGS. 8B and 8C are cross-sectional schematics of the inflatable tube shown in FIG. 8A, positioned within a representative blood vessel.

A schematic of an embodiment of a chemical ablation therapy delivery system is presented in FIGS. 8A-8C and is identified by reference numeral 330*d*. Corresponding components of one or more of the above-described systems and the system 330*d* of FIGS. 8A-8C are identified by a common reference numeral, and unless otherwise noted herein to the contrary the foregoing discussion of these corresponding components remains applicable to the system 330*d* of FIGS. 8A-8D.

The chemical ablation therapy delivery system 330*d* utilizes the above-noted guide catheter 302 (although the above-noted guide catheter 302' may be utilized), along with an ablation catheter 310*d*. The ablation catheter 310*d* includes a distal shaft 312*d* and an inflatable tube 316*d*. The distal shaft 312*d* includes a lumen 314*d* that is fluidly connected with an appropriate ablation agent source (e.g., ablation agent source 152 in FIG. 9, discussed below). For ease of illustration the inflatable tube 316*d* is rotated 90° relative to the distal shaft 312*d* in FIG. 8A. It should be appreciated that the catheter 180 of FIG. 3 may be adapted in accord with the ablation catheter 310*d* of FIGS. 8A-8C.

The inflatable tube 316*d* includes a first end 352*a* to which the lumen 314*d* extends (e.g., the first end 352*a* may be characterized as an "open end" of the inflatable tube 316*d*). A second end 352*b* of the inflatable tube 316*d* is spaced from the first end 352*a*. The inflatable tube 316*d* proceeds along an arcuate path from the first end 352*a* to the second end 352*b* when the inflatable tube 316*d* is in a deployed state or configuration (e.g., FIGS. 8A-8C). The inflatable tube 316*d* may be formed from a material or combination of materials so as to be at least one of flexible, elastic, expandable, and deformable. Representative materials for the inflatable tube 316*d* (and any balloon addressed herein) include without limitation nitinol, Pebax®, nylon, or polyamide.

The inflatable tube 316*d* may be characterized as including an outer sidewall 350*a* and an inner sidewall 350*b* that are each disposed about a center axis when the inflatable tube 316*d* is in its deployed configuration. The outer sidewall 350*a* and inner sidewall 350*b* each extend along an arcuate path proceeding between the first end 352*a* and the second end 352*b* of the inflatable tube 316*d*. In one embodiment the first end 352*a* and the second end 352*b* are radially spaced from one another (e.g., in the illustrated embodiment the inflatable tube 316*d* does not proceed a full 360° about this center axis in its deployed configuration; in the illustrated embodiment the inflatable tube 316*d* is not a circular structure in its deployed configuration).

The outer sidewall 350 includes one or more injectors 354 that are separately attached to the inflatable tube 316*d*. Any appropriate number of injectors 354 may be utilized, and any appropriate spacing may be utilized between each adjacent pair of injectors 354. Each injector 354 is fluidly interconnectable or is at all times fluidly interconnected with the interior of the inflatable tube 316*d*, and may be of any appropriate configuration. A given injector 354 may include one or more discharge ports, a given injector 354 may be in the form of the above-identified spike 342, or otherwise. In any case and when the inflatable tube 316*d* is in its fully deployed state or configuration (e.g., FIGS. 8A-8C), the outer sidewall 350*a* of the inflatable tube 316*d* should be disposed in interfacing relation with a corresponding portion of an inner wall 86 that defines a vessel 84 in which the ablation catheter 310*d* is disposed. Disposing the outer sidewall 350*a* of the inflatable tube 316*d* in its deployed state or configuration should dispose each injector 354 against the vessel wall 86 and/or through the vessel wall 86. An ablation agent or combination of ablation agents may be directed through injector 354 to provide for an extravascular chemical ablation at one or more targeted locations.

Figure 8D:
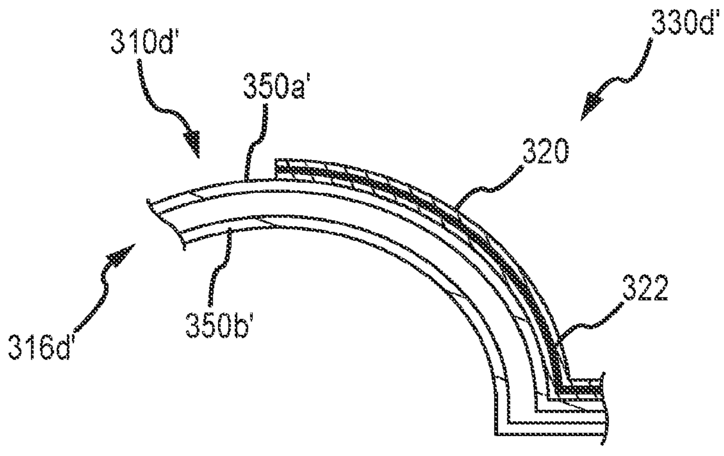
FIG. 8D is variation of the chemical ablation therapy delivery system shown in FIG. 8A, that utilizes a guide tube that is attached to the inflatable tube and through which an ablation agent needle may be deployed.

A schematic of a variation of the chemical ablation therapy delivery system 330*d* of FIGS. 8A-8C is presented in FIG. 8D and is identified by reference numeral 330*d'*. Corresponding components of the system 330*d* (FIGS. 8A-8C) and the system 330*d'* (FIG. 8D) are identified by a common reference numeral, and unless otherwise noted herein to the contrary the foregoing discussion of these corresponding components remains applicable to the system 330*d'* of FIG. 8D. Instead of using one or more injectors 354, the ablation catheter 310' of FIG. 8D uses one or more of the above-noted guide tubes 320, again where each guide tube 320 has a corresponding ablation needle 322. In the illustrated embodiment a guide tube 320 and corresponding ablation needle 322 are shown as being mounted on the outer sidewall 350*a'* of the inflatable tube 316*d'*. However, a guide tube 320 and its corresponding ablation needle 322 could be disposed between the outer sidewall 350*a'* and the inner sidewall 350*b'* of the inflatable tube 316*d'*, with the guide tube 320 being attached to the outer sidewall 350*a'* (e.g., in accord with FIG. 4D).

Figure 9:
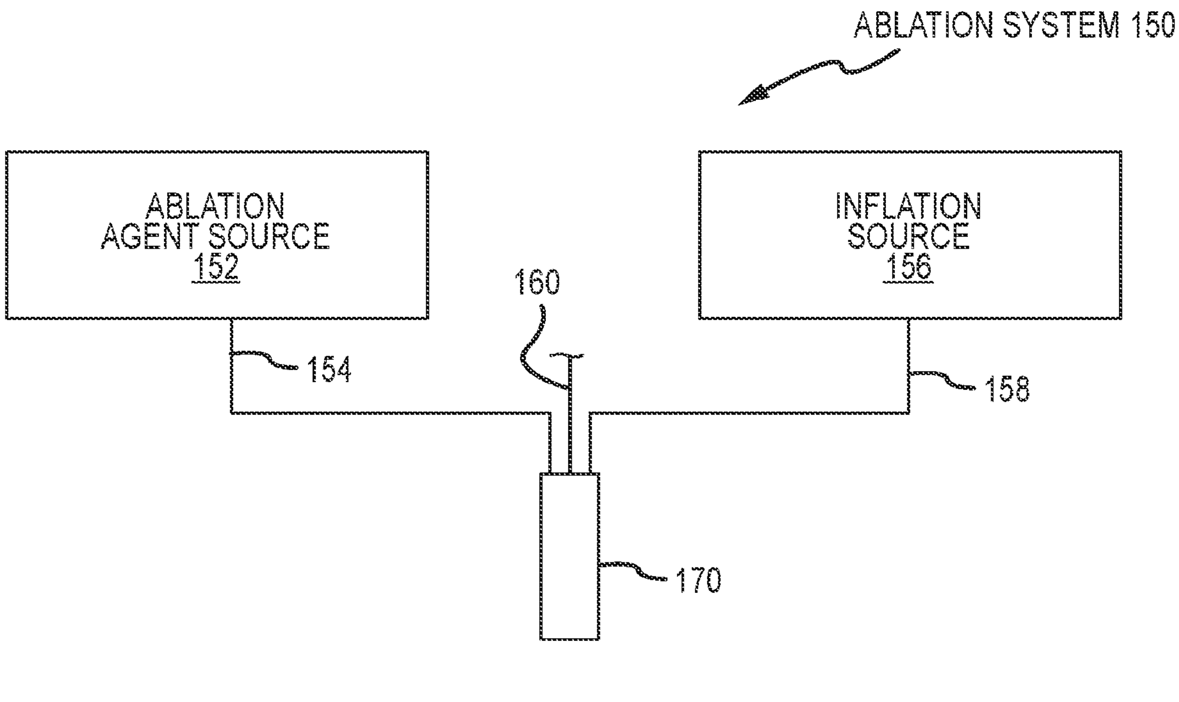
FIG. 9 is a schematic of an ablation system that includes an ablation source and an optional inflation source that are associated with an expandable element.

A schematic of an ablation system is illustrated in FIG. 9 and is identified by reference numeral 150. Components of the ablation system 150 include an ablation agent source 152, a first feed line 154 extending from the ablation agent source 152 to an expandable element 170, an inflation source 156, a second feed line 158 extending from the inflation source 156 to the expandable element 170, and an exhaust line 160 that extends from the interior of the expandable element 170 (when in the form of a balloon) to a location outside of the expandable element 170. Each of the lines 154, 158, and 160 include a lumen to accommodate a corresponding flow. The expandable element 170, the first feed line 154, the second feed line 158, and the exhaust line 160 may be incorporated by an ablation catheter in accordance with the foregoing. In this regard, the ablation agent source 152 may use any appropriate ablation agent or combination of ablation agents (e.g., $CaCl_2$, ethanol) for the various ablation catheters addressed herein, in any appropriate form (e.g., liquid, powder, or solid), or both.

In the case where the expandable element 170 shown in FIG. 9 is in the form of a stent, and for the various ablation catheters addressed herein that may utilize such a stent, the inflation source 156 and second feed line 158 need not be utilized. In the embodiments of FIGS. 4A-4D and FIG. 8D, each inflation needle 322 may be fluidly connected with the ablation agent source 152. In the embodiments of FIGS. 5A-5C, FIGS. 6A-6B, and FIG. 7, each conduit 340 may be fluidly connected with the ablation agent source 152. In the case of the ablation catheter 310*d* of FIGS. 8A-8C, the ablation agent source 152 may be used to inflate the inflatable tube 310*d* (e.g., the inflation source 156 and second feed line 158 need not be utilized in this instance).

Further disclosed herein is the subject-matter of the following clauses:

1. A chemical ablation therapy delivery system, comprising:
   an expandable element;
   a guide tube attached to said expandable element; and
   a needle movably disposed within said guide tube.
2. The system of clause 1, wherein said guide tube is attached to said expandable element such that at least part of said guide tube is always maintained in a fixed position relative to said expandable element.
3. The system of any of the preceding clauses, wherein said guide tube extends within an interior of said expandable element.
4. The system of clause 3, wherein said guide tube extends from said interior toward a perimeter wall of said expandable element and is attached to said perimeter wall of said expandable element.
5. The system of clause 1 or 2, wherein said guide tube is disposed entirely exteriorly of said expandable element, and/or wherein said guide tube extends along an exterior of said expandable element.
6. The system of any of clauses 1, 2 or 5, wherein said expandable element is selected from the group consisting of a balloon and a stent.
7. The system of any of the preceding clauses, wherein said expandable element comprises a first expandable element and a second expandable element, wherein said second expandable element is disposed about said first expandable element, and wherein said guide tube is disposed between said first expandable element and said second expandable element and is attached to said second expandable element.
8. The system of clause 7, wherein said first expandable element and said second expandable element are each in the form of a balloon.
9. The system of clause 1 or 2, wherein said expandable element is in the form of an inflatable tube comprising a first end, a second end spaced from said first end, an outer sidewall that extends between said first end and said second end, and an inner sidewall that extends between said first end and said second end.
10. The system of clause 9, wherein said inflatable tube proceeds along an arcuate path from said first end to said second end when said inflatable tube is in a deployed configuration.
11. The system of clause 10, said outer sidewall and said inner sidewall of said inflatable tube are disposed about a center axis when said inflatable tube is in said deployed configuration, and wherein said first end and said second end are radially spaced from one another, relative to and about said center axis.
12. The system of any of clauses 9-11, wherein said guide tube extends along an exterior of said outer sidewall of said inflatable tube.
13. The system of any of the preceding clauses, wherein said needle is movable relative to said guide tube between a delivery position and a deployed position, and wherein said needle is entirely retained within said guide tube when in said delivery position and extends beyond said guide tube when in said deployed position.
14. The system of any of the preceding clauses, further comprising an ablation source interconnected with said needle, wherein said ablation source optionally comprises at least one ablation agent.
15. The system of any of the preceding clauses, further comprising a plurality of said guide tubes and a corresponding plurality of said needles, wherein each said guide tube has a corresponding said needle.
16. The system of clause 15, wherein each of said plurality of guide tubes comprises an exit and said expandable element comprises a central axis that corresponds with a length dimension of said expandable element.
17. The system of clause 16, wherein said exit of at least some of said plurality of guide tubes are disposed at different radial positions relative to and about said central axis of said expandable element, or wherein said exit of at least some of said plurality of guide tubes are disposed at different positions along a length of said expandable element.
18. A chemical ablation therapy delivery system, comprising:
   an expandable element; and
   a fluid delivery tube fixed to said expandable element; and
   an injector that extends from an outer perimeter of said fluid delivery tube, is at least fluidly connectable with an interior of said fluid delivery tube, and protrudes beyond an outer perimeter of said expandable element.
19. A chemical ablation therapy delivery system, comprising:
   an inflatable tube comprising a first end, a second end spaced from said first end, an outer sidewall that extends between said first end and said second end, and an inner sidewall that extends between said first end and said second end;
   an injector separately attached to said inflatable tube, wherein said injector is at least fluidly connectable with an interior space of said inflatable tube.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended clauses be construed to include alternative embodiments to the extent permitted by the prior art.

Any feature of any other various aspects addressed in this disclosure that is intended to be limited to a "singular" context or the like will be clearly set forth herein by terms such as "only," "single," "limited to," or the like. Merely introducing a feature in accordance with commonly accepted antecedent basis practice does not limit the corresponding feature to the singular. Moreover, any failure to use phrases such as "at least one" also does not limit the corresponding feature to the singular. Use of the phrase "at least substantially," "at least generally," or the like in relation to a particular feature encompasses the corresponding characteristic and insubstantial variations thereof (e.g., indicating that a surface is at least substantially or at least generally flat encompasses the surface actually being flat and insubstantial variations thereof). Finally, a reference of a feature in conjunction with the phrase "in one embodiment" does not limit the use of the feature to a single embodiment.

The invention claimed is:

1. A chemical ablation therapy delivery system, comprising: a first expandable element; a second expandable element disposed about and circumferentially surrounding the first expandable element; a guide tube disposed between an outer surface of the first expandable element and an inner surface of the second expandable element, wherein the guide tube extends through the second expandable element and is attached to the second expandable element; and a needle movably disposed within the guide tube, including being movably disposed within a portion of the guide tube disposed between the first expandable element and the second expandable element.

2. The system of claim 1, wherein the guide tube is attached to the second expandable element such that at least part of the guide tube is always maintained in a fixed position relative to the second expandable element.

3. The system of claim 1, wherein the first expandable element or the second expandable element is selected from the group consisting of a balloon and a stent.

4. The system of claim 1, wherein the first expandable element and the second expandable element are each in the form of a balloon.

5. The system of claim 1, wherein the first expandable element or the second expandable element is in the form of an inflatable tube comprising a first end, a second end spaced from the first end, an outer sidewall that extends between the first end and the second end, and an inner sidewall that extends between the first end and the second end.

6. The system of claim 1, wherein the needle is movable relative to the guide tube between a delivery position and a deployed position, and wherein the needle is entirely retained within the guide tube when in the delivery position and extends beyond the guide tube when in the deployed position.

7. The system of claim 1, further comprising an ablation source interconnected with the needle, wherein the ablation source comprises at least one ablation agent.

8. The system of claim 1, further comprising a plurality of guide tubes and a corresponding plurality of needles, wherein the plurality of guide tubes includes the guide tube and the plurality of needles includes the needle.

9. The system of claim 8, wherein each guide tube of the plurality of guide tubes comprises an exit and the first expandable element or the second expandable element comprises a central axis that corresponds with a length dimension of the first expandable element or the second expandable element.

10. The system of claim 9, wherein the exit of at least some guide tubes of the plurality of guide tubes are disposed at different radial positions relative to and about the central axis of the first expandable element or the second expandable element, or wherein the exit of at least some guide tubes of the plurality of guide tubes are disposed at different positions along a length of the first expandable element or the second expandable element.

11. A chemical ablation therapy delivery system, comprising: a first expandable element; a second expandable element disposed about and circumferentially surrounding the first expandable element; and a fluid delivery tube fixed to the second expandable element, wherein the fluid delivery tube is disposed between an outer surface of the first expandable element and an inner surface of the second expandable element, and wherein the fluid delivery tube extends through the second expandable element and is attached to the second expandable element; and an injector that is extendable from the fluid delivery tube, is at least fluidly connectable with an interior of the fluid delivery tube, and is capable of protruding beyond an outer perimeter of the second expandable element.

12. A chemical ablation therapy delivery system, comprising: a guide tube comprising a first end, and a second end spaced from the first end, wherein the guide tube is disposed between an outer surface of a first expandable element and an inner surface of a second expandable element circumferentially surrounding the first expandable element, and wherein the guide tube extends through the second expandable element and is attached to the second expandable element; and an injector movably disposed within the guide tube, including being movably disposed within a portion of the guide tube disposed between the first expandable element and the second expandable element.

* * * * *